(12) United States Patent
Rabinovitz et al.

(10) Patent No.: US 7,938,775 B2
(45) Date of Patent: May 10, 2011

(54) DEVICE, SYSTEM, AND METHOD FOR IN-VIVO ANALYSIS

(75) Inventors: Elisha Rabinovitz, Haifa (IL); Gavriel J. Iddan, Haifa (IL)

(73) Assignee: Given Imaging, Ltd., Yoqneam (IL)

( * ) Notice: Subject to any disclaimer, the term of this patent is extended or adjusted under 35 U.S.C. 154(b) by 868 days.

(21) Appl. No.: 11/631,017

(22) PCT Filed: Jun. 28, 2005

(86) PCT No.: PCT/IL2005/000686
§ 371 (c)(1),
(2), (4) Date: Dec. 28, 2006

(87) PCT Pub. No.: WO2006/001020
PCT Pub. Date: Jan. 5, 2006

(65) Prior Publication Data
US 2008/0294023 A1 Nov. 27, 2008

Related U.S. Application Data

(60) Provisional application No. 60/582,819, filed on Jun. 28, 2004.

(51) Int. Cl.
*A61B 5/00* (2006.01)

(52) U.S. Cl. ........ 600/309; 600/101; 600/109; 600/117; 600/118; 600/130; 600/160; 600/302; 600/407; 600/476; 600/582; 600/584

(58) Field of Classification Search .................. 600/407, 600/302, 101, 109, 117, 118, 130, 160, 476, 600/582, 584
See application file for complete search history.

(56) References Cited

U.S. PATENT DOCUMENTS
4,017,261 A  4/1977  Svoboda et al.
(Continued)

FOREIGN PATENT DOCUMENTS
DE  344 0177  6/1986
(Continued)

OTHER PUBLICATIONS

O. Olsvik, T. Popovic, E. Skjerve, K.S. Cudjoe, E. Hornes, J. Ugelstad, M. Uhlen, "Magnetic Separation Techniques in Diagnostic Microbiology", Jan. 1994, Clincal Microbiology Reviews, vol. 7, No. 1, pp. 43-54.*

(Continued)

*Primary Examiner* — Tse Chen
*Assistant Examiner* — Jason Ip
(74) *Attorney, Agent, or Firm* — Pearl Cohen Zedek Latzer, LLP

(57) ABSTRACT

A device, system and method for in-vivo analysis. An autonomous in-vivo device may include a magnet to detain at least a portion of a sample collected from a body lumen; a sensor to sense a property of the detained sample portion; and a transmitter to transmit data of the sensed property.

21 Claims, 4 Drawing Sheets

U.S. PATENT DOCUMENTS

| | | | |
|---|---|---|---|
| 4,278,077 | A | 7/1981 | Mizumoto |
| 5,114,864 | A | 5/1992 | Walt |
| 5,604,531 | A | 2/1997 | Iddan et al. |
| 5,716,595 | A * | 2/1998 | Goldenberg ............... 424/1.49 |
| 5,736,405 | A | 4/1998 | Alfano et al. |
| 5,928,159 | A | 7/1999 | Eggers et al. |
| 5,993,378 | A | 11/1999 | Lemelson |
| 6,159,445 | A | 12/2000 | Klaveness et al. |
| 6,240,312 | B1 * | 5/2001 | Alfano et al. ............... 600/476 |
| 6,324,418 | B1 | 11/2001 | Crowley et al. |
| 6,958,034 | B2 | 10/2005 | Iddan |
| 2001/0051766 | A1 | 12/2001 | Gazdzinski |
| 2002/0103417 | A1 | 8/2002 | Gazdzinski |
| 2002/0111544 | A1 * | 8/2002 | Iddan ............... 600/310 |
| 2002/0177779 | A1 | 11/2002 | Adler et al. |
| 2004/0092825 | A1 * | 5/2004 | Madar et al. ............... 600/473 |

FOREIGN PATENT DOCUMENTS

| | | |
|---|---|---|
| JP | 4-109927 | 4/1992 |
| JP | 1992-144533 | 5/1992 |
| JP | 05200015 A * | 8/1993 |
| WO | WO 01/65995 | 9/2001 |

OTHER PUBLICATIONS

Davies, et al.: Detection of the Cancer-Prone Colon, Using Transepithelial Impedence Analysis, Arch Surg, vol. 124, Apr. 1989, pp. 480-448.

Park et al.: "A Technique for Position Detection of miniatured Wireless Telemetry Module in the Human Body", Proceedings of the $32^{nd}$ ISR (International Symposium on Robotics), Apr. 19-21. 2001, pp. 1888-1892.

Blad, B. et al.: "Impedance spectra of tumor tissue in comparison with normal tissue: a possible clinical application for electrical tomography", Physiological Measurements, vol. 17, Nov. 1996, pp. 105-115.

Muretto, P., et al: "An endogastric capsule for measuring tumor markers in gastric juice: an evaluation of the safety and efficacy of a new diagnostic tool", Ann Oncol., Jan. 2003, 14(1), pp. 105-109.

International Search Report for International Application No. PCT/IL05/006813, completed on Nov. 1, 2006.

* cited by examiner

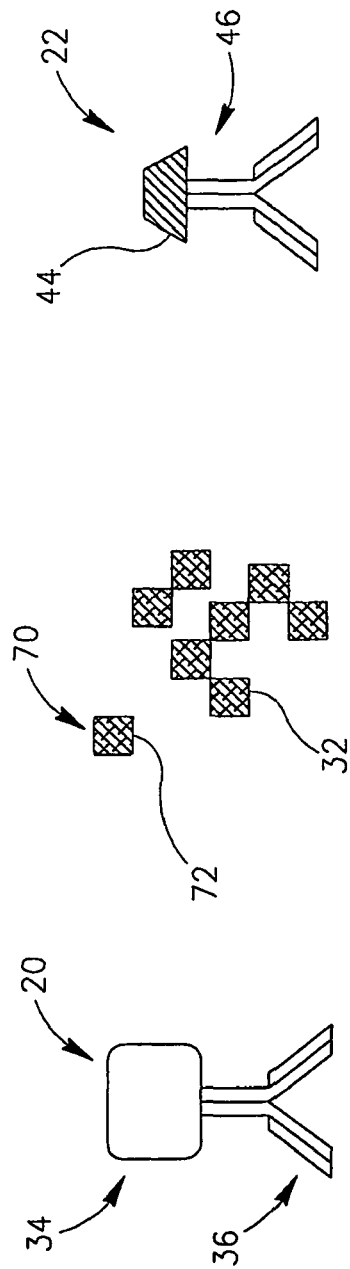
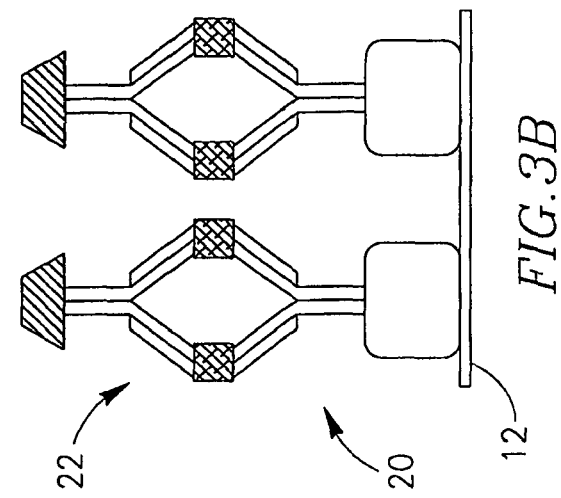
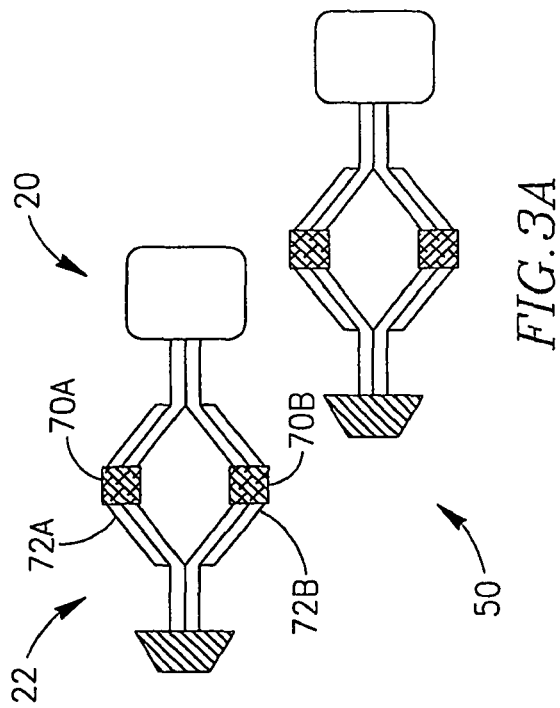

DEVICE, SYSTEM, AND METHOD FOR IN-VIVO ANALYSIS

PRIOR APPLICATION DATA

The present application is a national phase application of International Application No. PCT/IL2005/000686, entitled "DEVICE, SYSTEM, AND METHOD FOR IN-VIVO ANALYSIS", with international filing date, Jun. 28, 2005, which in turn claims priority from U.S. Provisional Application 60/582,819, filed on Jun. 28, 2004, all of which are incorporated by reference in their entirety.

FIELD OF THE INVENTION

The present invention relates to the field of in-vivo sensing and imaging.

BACKGROUND OF THE INVENTION

An atypical concentration or presence of substances in body fluids or in body lumens may be indicative of the biological condition of the body. For example, the presence of elevated concentrations of red blood cells in the gastrointestinal (GI) tract may indicate different pathologies, depending on the location of the bleeding along the GI tract. Similarly, abnormalities in physical conditions of the body, e.g., elevated temperature, may indicate a pathology. Early detection, identification and location of abnormal conditions may aid in correctly diagnosing and treating various pathologies.

Medical detection kits may be based on in-vitro testing of body fluid samples for the presence of a suspected substance. The in-vitro method of detection may not easily allow localization or identification of the origin of an abnormally occurring substance. In some instances, localizing an abnormally occurring substance in a body may contribute to the identification of a pathology, and thus may contribute to the facile treatment of the identified pathology. For example, bleeding in the stomach may indicate an ulcer, whereas bleeding in the small intestine may indicate the presence of a tumor.

In some cases, diseases, e.g., cancer, may be detected by analyzing the blood stream for tumor specific markers, for example, specific antibodies. A drawback of this method is that the appearance of antibodies in the blood stream may usually occur at a late stage of the disease, such that early detection is not possible using this method.

Detection of pathologies in the GI tract may be performed using endoscopy, but this method may be limited to the upper or lower gastrointestinal tract. Thus, pathologies in other parts of the GI tract, such as the small intestine, may not be easily detected using endoscopy.

SUMMARY OF THE INVENTION

Various embodiments of the invention provide, for example, devices, systems and methods of in-vivo analysis.

In some embodiments, for example, an autonomous in-vivo device may include a magnet to detain, retain, hold and/or aggregate at least a portion of a sample collected from a body lumen; a sensor to sense a property of the detained sample portion; and a transmitter to transmit data of the sensed property.

In some embodiments, for example, the in-vivo device may include an inlet to transfer the sample into the autonomous in-vivo device.

In some embodiments, for example, the in-vivo device may include a duct to transfer the sample within the autonomous in-vivo device.

In some embodiments, for example, the in-vivo device may include a micropump to pump in the sample into the autonomous in-vivo device.

In some embodiments, for example, the in-vivo device may include a magnetized reagent, e.g., having a magnetized antibody, for example, to be mixed with the sample within the autonomous in-vivo device.

In some embodiments, for example, the in-vivo device may include a magnetized antibody to be mixed with the sample within the autonomous in-vivo device. In some embodiments, for example, the in-vivo device may include a detector antibody to be mixed with the sample within the autonomous in-vivo device; the detector antibody may optionally include a color label or colorant.

In some embodiments, for example, the in-vivo device may include an outlet to transfer out of the autonomous in-vivo device a portion of the sample not detained by the magnet.

In some embodiments, for example, the in-vivo device may include an illumination source to illuminate the detained portion, and the sensor may include an imager to acquire in-vivo an image of the detained portion.

In some embodiments, for example, the in-vivo device may include a reservoir to store a substance to be mixed with the sample; the substance may be, for example, a magnetized reagent, a magnetized antibody, a detector antibody, a detector antibody having a colorant, or the like.

In some embodiments, for example, the in-vivo device may include an imager to acquire an in-vivo image of the body lumen.

In some embodiments, for example, the in-vivo device may be or may include a swallowable capsule.

In some embodiments, an in-vivo system may include, for example, an in-vivo device including at least a magnet to detain a portion of a sample collected from a body lumen, and an in-vivo sensor to sense a property of the detained sample portion; and a receiver to receive sensed data transmitted from the in-vivo device. In some embodiments of the in-vivo system, the in-vivo device may include, for example, a transmitter to transmit the sensed data.

In some embodiments of the in-vivo system, the in-vivo device may include, for example, an in-vivo imager to acquire an image of the detained sample portion; and a transmitter to transmit the image data.

In some embodiments of the in-vivo system, the in-vivo device may include, for example, a reservoir to store a substance to be mixed with the sample; the substance may be, for example, a magnetized reagent, a magnetized antibody, a detector antibody, a detector antibody having a colorant, or the like.

A method in accordance with some embodiments of the invention may optionally include, for example, collecting in-vivo a sample from a body lumen; detaining the sample in-vivo using magnetic force; sensing in-vivo a property of the detained sample; and transmitting data of the sensed property.

A method in accordance with some embodiments of the invention may optionally include, for example, mixing in-vivo a magnetized antibody into the sample.

A method in accordance with some embodiments of the invention may optionally include, for example, aggregating magnetized antibodies in proximity to an in-vivo magnetic element.

A method in accordance with some embodiments of the invention may optionally include e, for example, acquiring in-vivo an image of the detained sample.

A method in accordance with some embodiments of the invention may optionally include, for example, acquiring in-vivo an image of the body lumen.

A method in accordance with some embodiments of the invention may optionally include, for example, analyzing in-vivo the detained sample.

Some embodiments may include, for example, an in-vivo device which may be autonomous and/or may include a swallowable capsule.

Embodiments of the invention may allow various other benefits, and may be used in conjunction with various other applications.

BRIEF DESCRIPTION OF THE DRAWINGS

The subject matter regarded as the invention may be particularly pointed out and distinctly claimed in the concluding portion of the specification. The invention, however, both as to organization and method of operation, together with objects, features and advantages thereof, may best be understood by reference to the following detailed description when read with the accompanied drawings in which:

FIG. 2 is a schematic illustration of components of magnetic antigen detection according to an embodiment of the invention;

FIGS. 3A and 3B are schematic illustrations of components of magnetic antigen detection operative according to an embodiment of the invention;

Figure 1:
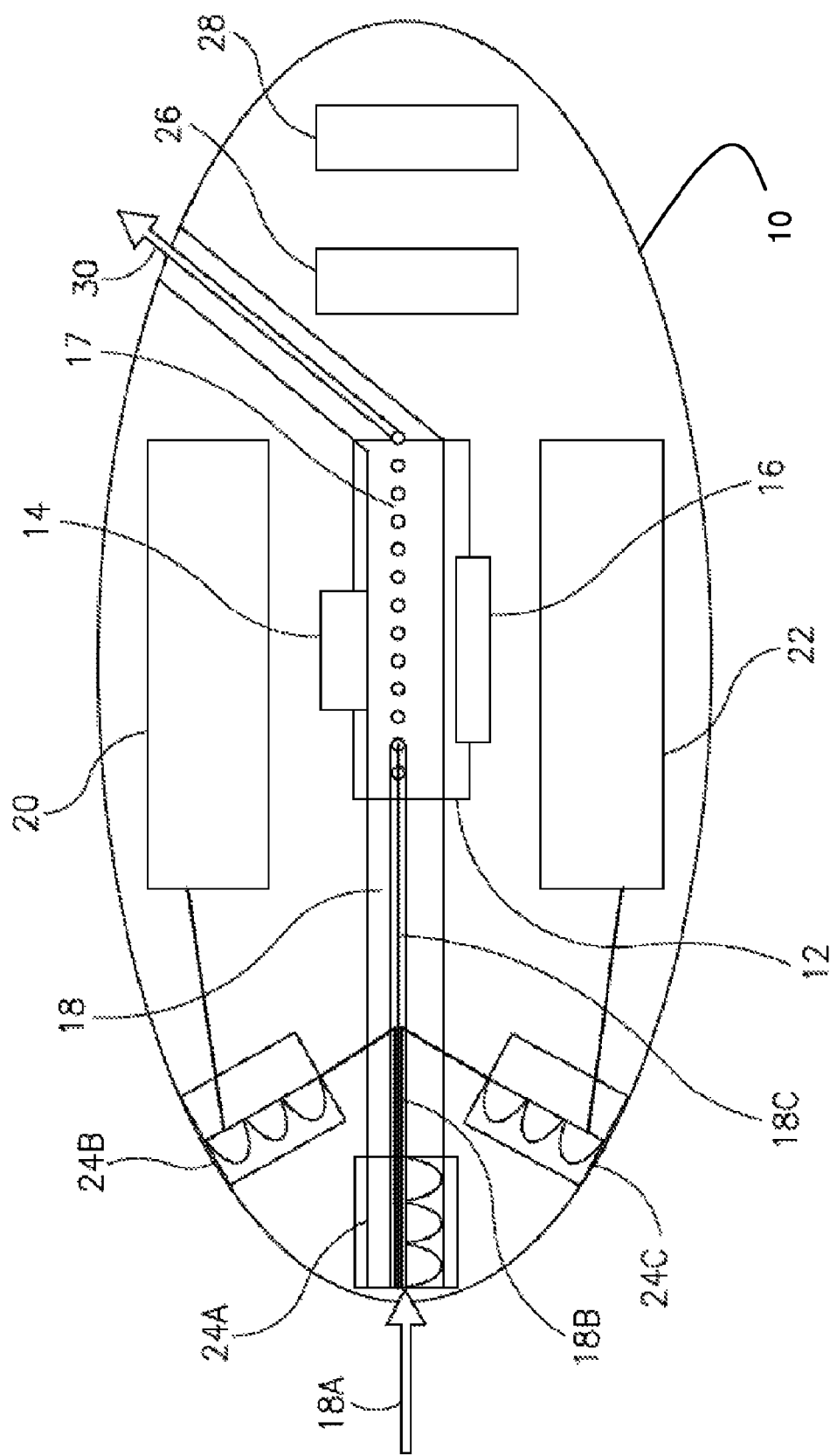
FIG. 1 is a schematic, longitudinal cross-section illustration of an in-vivo device, constructed and operative in accordance with an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

Various examples are given throughout this description. These are merely descriptions of specific embodiments of the invention, but the scope of the invention is not limited to the examples given. Features described with respect to one embodiment may be included in other embodiments though not described therein. Aspects of the various embodiments disclosed herein are combinable with the other embodiments disclosed herein.

It should be noted that although a portion of the discussion may relate to in-vivo imaging devices, systems, and methods, the present invention is not limited in this regard, and embodiments of the present invention may be used in conjunction with various other in-vivo sensing devices, systems, and methods. For example, some embodiments of the invention may be used, for example, in conjunction with in-vivo sensing of pH, in-vivo sensing of temperature, in-vivo sensing of pressure, in-vivo sensing of electrical impedance, in-vivo detection of a substance or a material, in-vivo detection of a medical condition or a pathology, in-vivo acquisition or analysis of data, and/or various other in-vivo sensing devices, systems, and methods. Some embodiments of the invention may be used not necessarily in the context of in-vivo imaging or in-vivo sensing.

Some embodiments of the present invention are directed to a typically swallowable in-vivo sensing device, e.g., a typically swallowable in-vivo imaging device. Devices according to embodiments of the present invention may be similar to embodiments described in U.S. patent application Ser. No. 09/800,470, entitled "Device And System For In-vivo Imaging", filed on 8 Mar. 2001, published on Nov. 1, 2001 as United States Patent Application Publication Number 2001/0035902, and/or in U.S. Pat. No. 5,604,531 to Iddan et al., entitled "In-Vivo Video Camera System", and/or in U.S. patent application Ser. No. 10/046,541, filed on Jan. 16, 2002, published on Aug. 15, 2002 as United States Patent Application Publication Number 2002/0109774, all of which are hereby incorporated by reference. An external receiving unit and processor, such as in a work station, such as those described in the above publications could be suitable for use with embodiments of the present invention. Devices and systems as described herein may have other configurations and/or other sets of components. For example, the present invention may be practiced using an endoscope, needle, stent, catheter, etc.

Reference is made to FIG. 1, which depicts an in-vivo device 10, which may be implemented as, for example, a swallowable capsule; device 10 may take other forms, and need not be swallowable or a capsule. Device 10 may include one or more magnetic elements or magnets 12 and magnetized species or other species that may be attracted to a magnet and reagents to react with specific antigens, if present, in an endoluminal body fluid analyte sample. In some embodiments, magnet(s) 12 may include, for example, a permanent magnet, a magnetic element, a magnetic coil, an electromagnetic element or coil, or the like. According to some embodiments, magnets 12 may include, for example, rare earth magnets such as, for example, neodymium magnets and/or samarium-cobalt magnets. According to some embodiments, ferrite magnets and/or platinum magnets, for example, may be used.

According to some embodiments, device 10 may include at least one analyte inlet 18A, which may be associated with, or may lead to, a duct 18 having, for example, sections 18B and 18C as shown, to allow analyte (e.g., possibly containing a specific antigen) to flow through in-vivo device 10. Other configurations for ducts, tubes or other carriers may be used.

According to an embodiment of the invention, device 10 may include one or more micropumps 24; for example, three micropumps 24A, 24B and 24C are shown, but other numbers may be used. Micropumps 24 may pump the analyte through inlet 18A, and/or may pump other reagents, e.g., magnetized reagents from a reservoir 20 and/or detector antibodies from a reservoir 22, into the sections of the duct 18. According to some embodiments, device 10 may include an outlet 30, e.g., associated with the duct 18, for example, to allow the analyte to exit the in-vivo device 10. Device 10 may further include an illumination source 14, e.g., one or more Light-Emitting Diodes (LEDs), a sensor or detector 16, a transmitter 26, and a power source 28. Other configurations and types of components are possible.

Transmitter 26 may include control capability, for example, to control the various operations of device 10; although control capability or one or more aspects of control may be included in a separate component. Transmitter 26 may be, for example, an Application Specific Integrated Circuit (ASIC), but may be of other constructions; for example, transmitter 26 may be a processor executing instructions. Device 10 may include a processing unit separate from transmitter 26 that may, for example, contain or process instructions.

Device 10 may be, or may include, an autonomous swallowable capsule, but device 10 may have other shapes and need not be swallowable and/or autonomous. Embodiments of device 10 are typically autonomous, and are typically self-contained. For example, device 10 may be a capsule or other unit where all the components are substantially contained within a container or shell or housing, and where device 10 does not require any wires or cables to, for example, receive power or transmit information. Device 10 may communicate with an external receiving and display system to provide display of data, control, or other functions. For example, power may be provided by an internal battery or using a wireless receiving system. Other embodiments may have other configurations and capabilities. For example, components may be distributed over multiple sites or units. Control information may be received from an external source.

Illumination source 14 may be used according to embodiments of the present invention to illuminate a portion of duct 18, for example, portion 17. According to some embodiments, illumination source 14, or other illumination sources, may be used to illuminate a body lumen. Sensor or detector 16 may sense or detect optical changes occurring at portion 17 of duct 18, which may typically be near (e.g., in proximity to) magnets 12, and transmitter 26 may transmit the output of sensor or detector 16 to an external receiving unit.

According to an embodiment of the invention, device 10 may optionally include reservoir 20 storing a magnetized antibody, and/or reservoir 22 storing a detector antibody. Reservoir 20 may be fluidly connected to portion 18B of duct 18, whereas reservoir 22 may be fluidly connected to portion 18C of duct 18. An analyte sample that may contain a specific antigen may enter the in-vivo device 10 through inlet 18A. The analyte may enter, e.g., through a gate such as one described in International Application Number PCT/IL 2005/000524, titled "Device, System and Method for In-Vivo Sampling", filed on May 22, 2005, which is hereby incorporated by reference. Other suitable gating mechanisms may be used.

The analyte may be pumped through micropump 24A to portion 18B. Meanwhile, magnetized antibody from reservoir 20 may be pumped, for example, through micropump 24B into portion 18B, where it may be mixed with the analyte that is already in portion 18B. The combined analyte and magnetized antibody may continue to travel along duct 18, arriving at portion 18C. According to some embodiments, at generally or approximately the same time, detector antibody from reservoir 22 may be pumped, for example, through micropump 24C into portion 18C and mixed with the combination of analyte and magnetized antibody that was pumped through to portion 18C.

According to other embodiments, pumps or micropumps need not be used, and reagents may be mixed by other possible methods. According to some embodiments, reagents, e.g., the magnetized antibody and/or the detector antibody, may be stored in duct 18, and need not be stored in separate or dedicated reservoirs.

The combining of the analyte sample and different reagent(s) may result in a mixture or a complex, for example, as further described with reference to FIGS. 2, 3A and/or 3B. The mixture of the analyte (e.g., which may contain a specific antigen), magnetized antibody and detector antibody may be pumped through inlet 18A, or may be otherwise moved through duct 18, for example, by capillary forces. At portion 17 the magnetized antibodies that are pumped or otherwise move through duct 18, may be drawn to magnet 12 by magnetic force, and may be detained, retained, held and/or aggregated at portion 17. Portion 17 may then be illuminated by illumination source 14, and optical changes occurring at portion 17 may be sensed or detected by sensor or detector 16.

According to some embodiments, sensor or detector 16 may be or may include, for example, a photodiode, a florescence device, an electrochemical sensing device, a magnetic field sensing device, a spectrophotometer, an image sensor, an imager; a Charge Coupled Device (CCD) camera or imager, a Complementary Metal Oxide Semiconductor (CMOS) camera or imager, a digital camera, a stills camera, a video camera, an optical analysis unit, an optical detector, an optical analysis instrument, a photo detector, or other suitable imagers, cameras, or image acquisition components. A detected image or other optical signal may be transmitted by transmitter 26 to an external receiver. The received image or other signal may be then analyzed, for example, for the presence of a specific antigen.

According to some embodiments, sensor or detector 16 may not be an optical detector, but rather may detect, for example, pH, temperature, voltage, conductivity, pressure, radioactivity, or other parameters, properties or characteristics. Reference is made to FIGS. 2, 3A and 3B which depict an antigen 32 which may be found in the analyte sample, a magnetized antibody 20, and detector antibody 22, respectively, according to some embodiments of the invention.

As shown in FIG. 2, magnetized antibody 20 may include, for example, a magnetic bead 34 which may be bound to a capture antibody 36. Other species may be bound to a capture antibody, such as ferromagnetic like particles, ferrite particles, or the like. Detector antibody 22 may include a label 44, such as ruthenium or other label capable of being detected by sensor or detector 16 of FIG. 1, bound to an antibody 46. Antigen 32, whose presence within the analyte is being tested, may have at least two binding sites 70 and 72, to bind certain antibodies to antigen 32. Antigen 32 may be or may include, for example, one or more tumor markers or other markers, e.g., CA 19-9, CEA, albumin, or the like; whereas detector antibody 22 may be or may include antibodies specific for the antigen 32. Label 44 may include a colorant, a fluorescent compound, a radioactive compound, an electrically charged species, or the like.

FIG. 3A illustrates magnetized antibody 20, detector antibody 22 and antigen 32 bound together into a complex formation 50 according to an embodiment of the invention. Magnetized antibody 20 is shown bound to antigen 32 at first binding site 70 (shown as 70A and 70B), whereas detector antibody 22 may be bound to antigen 32 at second binding site 72 (shown as 72A and 72B). The result may be complex formation 50. FIG. 3B further illustrates the capture of complex formation 50 according to an embodiment of the invention.

According to some embodiments, after a sample passes through micropump 24A of FIG. 1 and into portion 18B, the analyte may be introduced to magnetized antibody 20. If antigen 32 is present in the analyte, antigen 32 may bind with magnetized antibody 20 at first binding site 70 of FIG. 3A. The analyte sample, which may now include antigen 32 bound to magnetized antibody 20, may then continue along duct 18 of FIG. 1 into portion 18C, where it may be introduced to detector antibody 22. Antigen 32, if present in the analyte, may now bind detector antibody 46 at second binding site 72 of FIG. 3A. If all the components are bound together, complex formation 50 may be created.

Complex formation 50 may be detained, retained, held and/or aggregated in duct 18 using magnet 12, as complex formation 50 may include magnetic bead 34. For example, magnet 12 may be placed in proximity to portion 17, such that complex 50 may be detained at portion 17.

According to some embodiments, complex formation 50 may contain a colored label 44, such that an aggregation of complex 50 at portion 17 may result in the appearance of color or of another optical change or optical property in duct 18. For example, label 44 may include a charged particle, e.g., an electrochemical moiety or another particle, which upon aggregation may be detected by detector 16. In some embodiments, if antigen 32 is missing from the analyte sample, complex formation 50 will not be formed and, although magnetized antibody 20 may be detained, retained, held and/or aggregated at portion 17, its presence may not be detected. According to some embodiments, an aggregation of unbound magnetized antibody at portion 17 may be detected, but may be differentiated from bound magnetized antibody.

Figure 4:
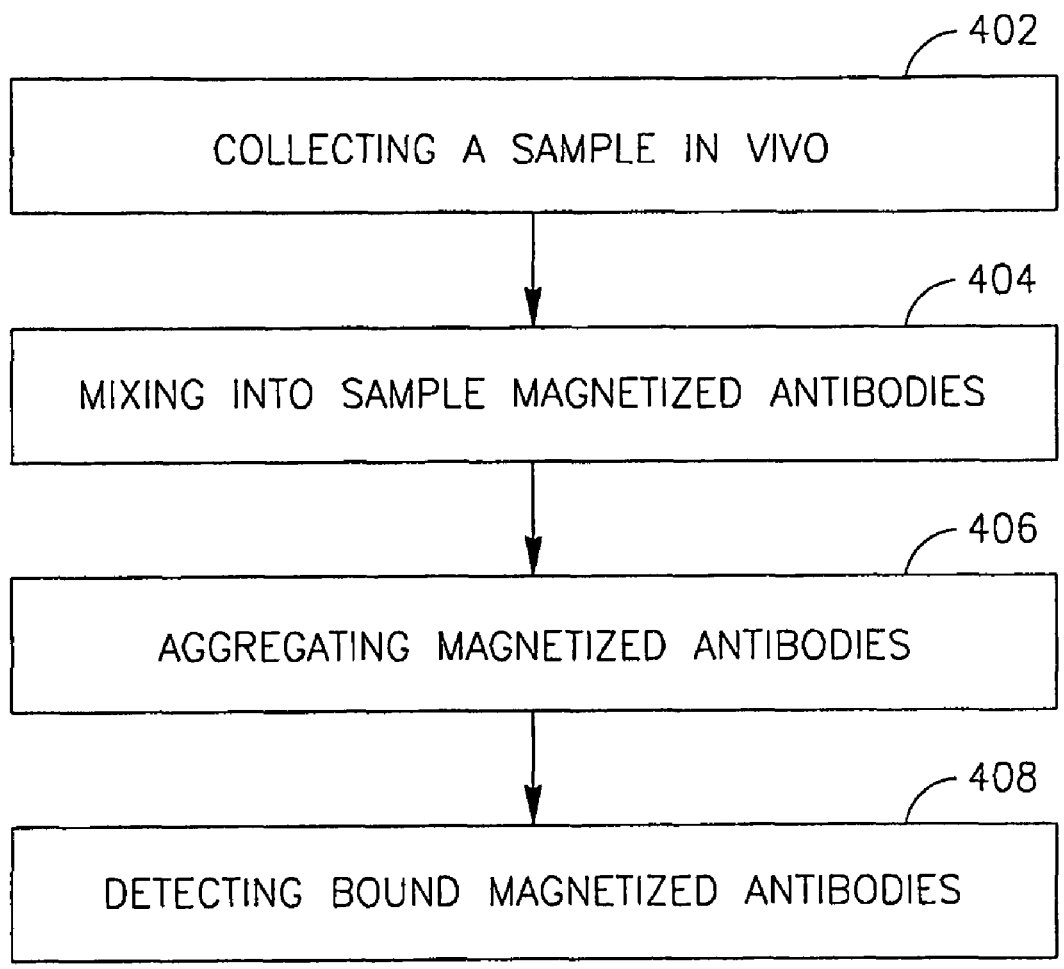
FIG. 4 is a flowchart diagram of a method of in-vivo analysis according to an embodiment of the invention.

Reference is now made to FIG. 4, which schematically depicts a flowchart of a method for in-vivo detection and/or analysis according to an embodiment of the invention. The method may be used, for example, in conjunction with one or more components of FIG. 1, FIG. 2, FIG. 3A, FIG. 3B, FIG. 5, and/or other suitable components.

As indicated at box 402, a sample may be collected in-vivo, e.g., utilizing an in-vivo device as described herein.

As indicated at box 404, the collected sample may be mixed with at least a magnetized antibody or other substance, for example, as described herein. Optionally, a second antibody may be mixed with the sample prior to, after or together with the mixing of the magnetized antibody. According to some embodiments, the second antibody may be bound to a colorant or other detecting means. More than one type of antibody may be mixed into the sample.

It is noted that the terms "antibody" or "antibodies" as used herein may include, for example, one or more substances, molecules and/or compounds, e.g., capable of specifically binding to a site, or a tumor marker or other component of an analyte. Other types of antibodies may be used.

As indicated at box 406, magnetized antibodies (or other suitable antibodies or substances) may be aggregated, held, detained or retained, for example, utilizing a magnet. Other means of aggregation may be used, e.g., using a ferromagnetic element.

As indicated at box 408, magnetized antibodies that have bound a component from the sample may be detected, sensed, imaged, measured and/or analyzed, e.g., thereby allowing analysis of the sample. For example, a detector may be directed to the area of aggregation, or may otherwise be in proximity or may touch the aggregation area, to allow sensing and/or imaging of aggregated magnetized antibodies.

According to some embodiments, a component from the sample may bind both a magnetized antibody and a second antibody which may include a detectable label. Aggregation of both types of antibodies may enhance the label, so that it may be detected by a detector. Other suitable operations or series of operations may be used.

Figure 5:
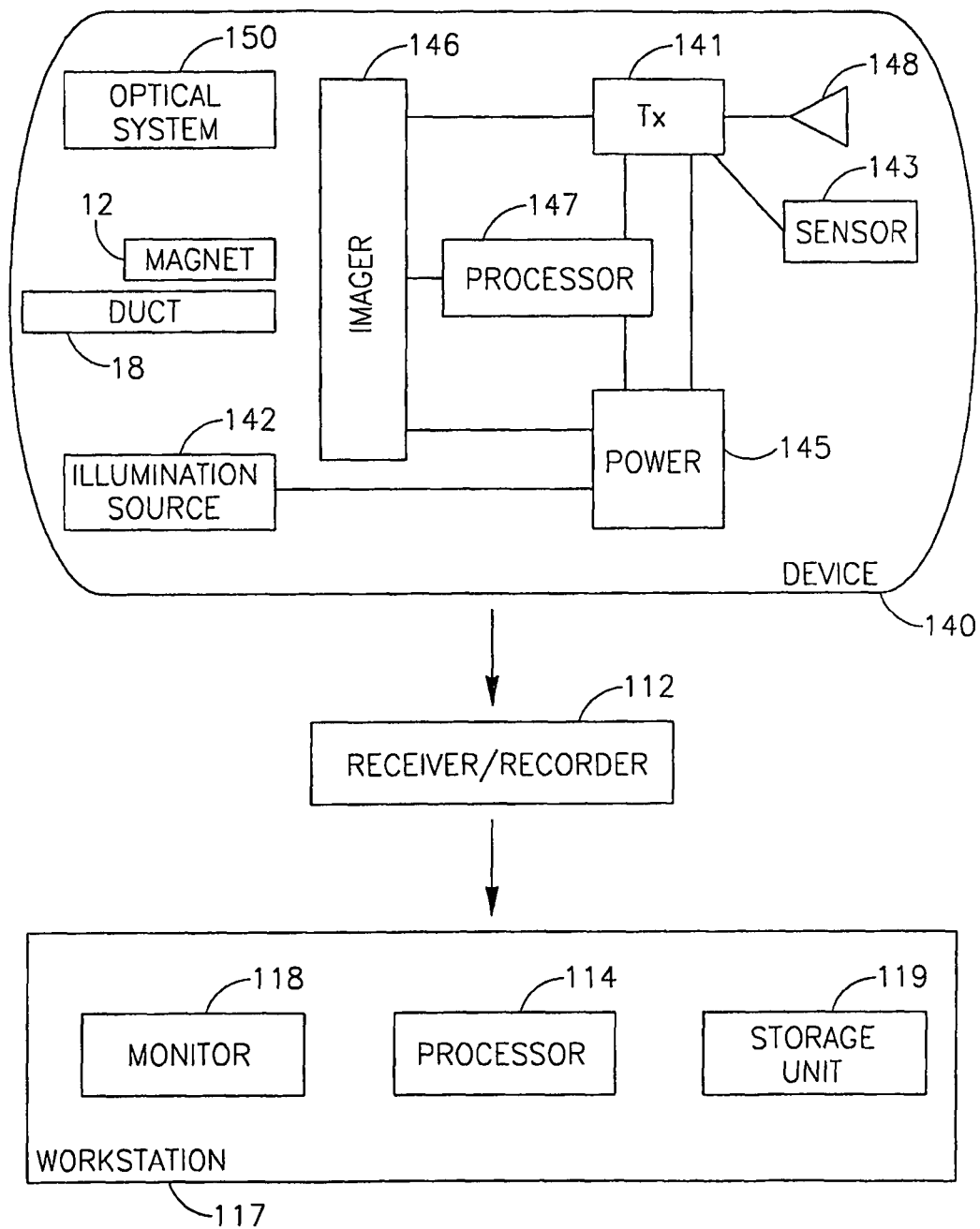
FIG. 5 is a schematic illustration of an in-vivo system in accordance with an embodiment of the invention.

FIG. 5 shows a schematic illustration of an in-vivo system in accordance with some embodiments of the present invention. One or more components of the system may be used in conjunction with, may be operatively associated with, the devices and/or components described above, or other in-vivo devices in accordance with embodiments of the invention.

In some embodiments, the system may include a device 140 having a sensor, e.g., an imager 146, one or more illumination sources 142, a power source 145, and a transmitter 141. In some embodiments, device 140 may be implemented using a swallowable capsule, but other sorts of devices or suitable implementations may be used. Outside a patient's body may be, for example, an external receiver/recorder 112 (including, or operatively associated with, for example, an antenna or an antenna array), a storage unit 119, a processor 114, and a monitor 118. In some embodiments, for example, processor 114, storage unit 119 and/or monitor 118 may be implemented as a workstation 117, e.g., a computer or a computing platform.

Transmitter 141 may operate using radio waves; but in some embodiments, such as those where device 140 is or is included within an endoscope, transmitter 141 may transmit/receive data via, for example, wire, optical fiber and/or other suitable methods. Other known wireless methods of transmission may be used. Transmitter 141 may include, for example, a transmitter module or sub-unit and a receiver module or sub-unit, or an integrated transceiver or transmitter-receiver.

Device 140 typically may be or may include an autonomous swallowable capsule, but device 140 may have other shapes and need not be swallowable or autonomous. Embodiments of device 140 are typically autonomous, and are typically self-contained. For example, device 140 may be a capsule or other unit where all the components are substantially contained within a container or shell, and where device 140 does not require any wires or cables to, for example, receive power or transmit information. In some embodiments, device 140 may be autonomous and non-remote-controllable; in another embodiment, device 140 may be partially or entirely remote-controllable.

In some embodiments, device 140 may communicate with an external receiving and display system (e.g., workstation 117 or monitor 118) to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

In some embodiments, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, imager 146 in device 140 may be operationally connected to transmitter 141. Transmitter 141 may transmit images to, for example, external transceiver or receiver/recorder 112 (e.g., through one or more antennas), which may send the data to processor 114 and/or to storage unit 119. Transmitter 141 may also include control capability, although control capability may be included in a separate component, e.g., processor 147. Transmitter 141 may include any suitable transmitter able to transmit image data, other sensed data, and/or other data (e.g., control data) to a receiving device. Transmitter 141 may also be capable of receiving signals/commands, for example from an external transceiver. For example, in some embodiments, transmitter 141 may include an ultra low power Radio Frequency (RF) high bandwidth transmitter, possibly provided in Chip Scale Package (CSP).

In some embodiment, transmitter 141 may transmit/receive via antenna 148. Transmitter 141 and/or another unit in device 140, e.g., a controller or processor 147, may include control capability, for example, one or more control modules, processing module, circuitry and/or functionality for controlling device 140, for controlling the operational mode or settings of device 140, and/or for performing control operations or processing operations within device 140. According to some embodiments, transmitter 141 may include a receiver which may receive signals (e.g., from outside the patient's body), for example, through antenna 148 or through a different antenna or receiving element. According to some embodiments, signals or data may be received by a separate receiving device in device 140.

Power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in-vivo device 140.

Optionally, in some embodiments, transmitter 141 may include a processing unit or processor or controller, for example, to process signals and/or data generated by imager 146. In another embodiment, the processing unit may be implemented using a separate component within device 140, e.g., controller or processor 147, or may be implemented as an integral part of imager 146, transmitter 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transmitter 141, and may be implemented, for example, using an ASIC.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optional optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminated light, and/or performing other light processing operations.

Data processor 114 may analyze the data received via external receiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In some embodiments, data processor 114 may be configured for real time processing and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In some embodiments, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to external receiver/recorder 112. Other constant and/or variable capture rates and/or transmission rates may be used.

Typically, the image data recorded and transmitted may include digital color image data; in alternate embodiments, other image formats (e.g., black and white image data) may be used. In some embodiments, each frame of image data may include 256 rows, each row may include 256 pixels, and each pixel may include data for color and brightness according to known methods. For example, a Bayer color filter may be applied. Other suitable data formats may be used, and other suitable numbers or types of rows, columns, arrays, pixels, sub-pixels, boxes, super-pixels and/or colors may be used.

Optionally, device 140 may include one or more sensors 143, instead of or in addition to a sensor such as imager 146. Sensor 143 may, for example, sense, detect, determine and/or measure one or more values of properties or characteristics of the surrounding of device 140. For example, sensor 143 may include a pH sensor, a temperature sensor, an electrical conductivity sensor, a pressure sensor, or any other known suitable in-vivo sensor. According to some embodiments, a sensor such as sensor 143 may be used to analyze (e.g., in-vivo) a sample in one or more of the suction chambers. For example, the pH of a sample may be sensed by a sensor on board the in-vivo device, and information from the sensor may be transmitted outside the body, for example, by transmitter 141 or by another transmitter receiving input from the sensor. In another embodiment, an in-vivo image sensor may be used to obtain color data (e.g., images) of a sample in a suction chamber. According to some embodiments, an imager on board the in-vivo device may image the suction chamber (and possibly a sample inside the suction chamber), and may transmit image data of the sample to an external receiver. In some embodiments, a body lumen and a sample may be imaged possibly simultaneously by the same imager, or separately using two imagers.

Device 140 may further include one or more components or mechanisms of any of FIGS. 1-4, or other in-vivo devices or systems in accordance with embodiments of the invention.

Such components may include, for example, one or more inlets, ducts, tubes, magnets, reservoirs, micropumps, various substances (e.g., analyte sample, magnetized reagent, detector antibody, or the like), outlets, or the like.

For example, in some embodiments, as shown in FIG. 5, device 140 may include duct 18 and magnet(s) 12 to detain, retain, hold and/or aggregate magnetized antibodies, e.g., for sensing, imaging or detection by imager 146, sensor 143, and/or other detector or sensor.

In some embodiments, in-vivo sensor 143 (or other suitable sensor) may sense or measure a property or characteristic of a content (e.g., a sample or substance) stored in a suction chamber, for example, temperature, pH, pressure, voltage, conductivity, optical quality, optical characteristic, color, brightness, hue, saturation, image, calorimetric characteristic, spectral characteristic, or the like.

Various aspects of the various embodiments disclosed herein are combinable with the other embodiments disclosed herein.

Although portions of the discussion herein may relate to an imager or an image sensor, embodiments of the invention are not limited in this regard; such imager or image sensor may include, for example, a detector, a sensor, a photodiode, a florescence device, an electrochemical sensing device, a magnetic field sensing device, a spectrophotometer, an image sensor, a Charge Coupled Device (CCD) camera or imager, a Complementary Metal Oxide Semiconductor (CMOS) camera or imager, a digital camera, a stills camera, a video camera, a light sensor; a device capable of detecting or sensing one or more colors, intensities, hues, brightness, contrast, and/or other parameters or characteristic; a device sensitive to one or more colors or able to detect one or more colors; a device capable of detecting one or more color changes; a device sensitive to color changes; or the like A device, system and method in accordance with some embodiments of the invention may be used, for example, in conjunction with a device which may be inserted into a human body. However, the scope of the present invention is not limited in this regard. For example, some embodiments of the invention may be used in conjunction with a device which may be inserted into a non-human body or an animal body.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An autonomous in-vivo device comprising:
   a magnetized reagent to be mixed, within said autonomous in-vivo device, with a sample collected from a body lumen;
   a detector reagent to be mixed, within said autonomous in-vivo device, with said sample;
      whereby particles within a first portion of said sample, which contains a substance to be detected by said detector reagent, bind to said magnetized reagent and to said detector reagent, and particles within a second portion of said sample, which does not contain the substance to be detected by said detector reagent, do not bind to said magnetized reagent and to said detector reagent;
   a magnet to detain said first portion of said sample, said magnet not detaining said second portion of said sample;
   a sensor to sense a property of the detained sample portion; and
   a transmitter to transmit data of the sensed property.

2. The autonomous in-vivo device of claim 1, comprising an inlet to transfer said sample into said autonomous in-vivo device.

3. The autonomous in-vivo device of claim 1, comprising a duct to transfer said sample within said autonomous in-vivo device.

4. The autonomous in-vivo device of claim 1, comprising a micropump to pump in said sample into said autonomous in-vivo device.

5. The autonomous in-vivo device of claim 1, wherein the magnetized reagent includes a magnetized antibody.

6. The autonomous in-vivo device of claim 1, wherein the detector reagent includes a detector antibody.

7. The autonomous in-vivo device of claim 6, wherein said detector antibody comprises a color label.

8. The autonomous in-vivo device of claim 1, comprising an outlet to transfer out of the autonomous in-vivo device a portion of said sample not detained by said magnet.

9. The autonomous in-vivo device of claim 1, comprising an illumination source to illuminate said detained portion, and wherein said sensor comprises an imager to acquire in-vivo an image of said detained portion.

10. The autonomous in-vivo device of claim 1, comprising a first reservoir to store said magnetized reagent and a second reservoir to store said detector reagent.

11. The autonomous in-vivo device of claim 1, comprising an imager.

12. The autonomous in-vivo device of claim 1, wherein said autonomous in-vivo device comprises a swallowable capsule.

13. A system comprising:
   an autonomous in-vivo device including at least
      a magnetized reagent to be mixed, within said autonomous in-vivo device, with a sample collected from a body lumen,
      a detector reagent to be mixed, within said autonomous in-vivo device, with said sample;
         whereby particles within a first portion of said sample, which contains a substance to be detected by said detector reagent, bind to said magnetized reagent and to said detector reagent, and particles within a second portion of said sample, which does not contain the substance to be detected by said detector reagent, do not bind to said magnetized reagent and to said detector reagent;
      a magnet to detain said first portion of said sample, said magnet not detaining said second portion of said sample;
      an in-vivo sensor to sense a property of the detained sample portion, and
      a transmitter to transmit data relating to the sensed property; and
   a receiver to receive the data relating to the sensed property transmitted from said in-vivo device.

14. The system of claim 13, wherein said in-vivo device comprises an in-vivo imager to acquire an image of the detained sample portion, and wherein said transmitter is to transmit the data relating to said image.

15. The system of claim 13, wherein said in-vivo device comprises a first reservoir to store said magnetized reagent and a second reservoir to store said detector reagent.

16. A method comprising:
   collecting in-vivo a sample from a body lumen into an autonomous in-vivo device;
   allowing said sample to be mixed with a magnetized reagent and with a detector reagent within said autonomous in-vivo device, such that particles within a first portion of said sample, which contains a substance to be detected by said detector reagent, bind to said magnetized reagent and to said detector reagent and particles within a second portion of said sample, which does not contain the substance to be detected by said detector reagent, do not bind to said magnetized reagent and to said detector reagent;

detaining said first portion of said sample within said autonomous in-vivo device using magnetic force and not detaining said second portion of said sample within said autonomous in-vivo device;

sensing within said autonomous in-vivo device a property of the detained sample portion; and transmitting data of the sensed property.

17. The method of claim 16, wherein detaining comprises: aggregating magnetized antibodies in proximity to an in-vivo magnetic element.

18. The method of claim 16, wherein sensing comprises: acquiring in-vivo an image of the detained sample portion.

19. The method of claim 16, comprising: acquiring in-vivo an image of said body lumen.

20. The method of claim 16, further comprising: analyzing in-vivo said detained sample portion.

21. The system of claim 13, wherein said detector reagent comprises a detector antibody.

* * * * *